United States Patent
Lifka et al.

(10) Patent No.: US 8,053,977 B2
(45) Date of Patent: Nov. 8, 2011

(54) LIGHT DEVICE AND METHOD OF MANUFACTURING A LIGHT DEVICE

(75) Inventors: Herbert Lifka, Eindhoven (NL);
Margreet De Kok, Eindhoven (NL);
Reinder Coehoorn, Eindhoven (NL);
Siebe Laurentius Maria Van Mensfoort, Eindhoven (NL)

(73) Assignee: Koninklijke Philips Electronics N V, Eindhoven (NL)

( * ) Notice: Subject to any disclaimer, the term of this patent is extended or adjusted under 35 U.S.C. 154(b) by 393 days.

(21) Appl. No.: 12/303,558

(22) PCT Filed: Jun. 1, 2007

(86) PCT No.: PCT/IB2007/052069
§ 371 (c)(1),
(2), (4) Date: Dec. 5, 2008

(87) PCT Pub. No.: WO2007/141720
PCT Pub. Date: Dec. 13, 2007

(65) Prior Publication Data
US 2010/0253225 A1    Oct. 7, 2010

(30) Foreign Application Priority Data
Jun. 7, 2006    (EP) .................................... 06115082

(51) Int. Cl.
*H05B 33/02* (2006.01)
(52) U.S. Cl. .......................................... 313/504; 445/24
(58) Field of Classification Search .................... 445/24; 313/504
See application file for complete search history.

(56) References Cited

U.S. PATENT DOCUMENTS

| 6,096,066 | A | 8/2000 | Chen |
| 6,290,713 | B1 | 9/2001 | Russell |
| 6,594,916 | B2 | 7/2003 | Boroson |
| 2003/0083622 | A1* | 5/2003 | Osawa et al. ............ 604/164.13 |
| 2003/0230752 | A1* | 12/2003 | Wu ................................. 257/81 |
| 2004/0166146 | A1 | 8/2004 | Holloway |
| 2005/0123676 | A1* | 6/2005 | Kuwahara et al. .............. 427/66 |
| 2006/0284551 | A1* | 12/2006 | Tsai et al. ..................... 313/506 |

FOREIGN PATENT DOCUMENTS

| WO | WO03043697 A2 | 5/2003 |
| WO | WO03050895 A1 | 6/2003 |
| WO | WO2006129223 A1 | 12/2006 |

OTHER PUBLICATIONS

Notten et al., "High energy density strategies: from hydride-forming materials research to battery integration," Journal of Power Sources 2004, vol. 129, Issue 1, pp. 45-54 teaches a lithylene battery technology.*

* cited by examiner

*Primary Examiner* — Toan Ton
*Assistant Examiner* — Hana Featherly
(74) *Attorney, Agent, or Firm* — Michael W. Haas

(57) ABSTRACT

Light device comprising a substrate, at least one photo-organic layer, at least two electrode layers electrically separated by said at least one photo-organic layer, and at least one encapsulation layer, wherein said at least one photo-organic layer is positioned between said substrate and said at least one encapsulating layer, and wherein multiple openings are provided that extend through the light device to allow fluids and or heat to pass through, said openings being spaced apart from said at least one photo-organic layer.

17 Claims, 3 Drawing Sheets

LIGHT DEVICE AND METHOD OF MANUFACTURING A LIGHT DEVICE

The invention relates to a light device, comprising a substrate, at least one photo-organic layer and at least two electrode layers.

The invention also relates to a method of manufacturing a light device.

Light, particularly IR and/or red light, has beneficial effects on the human body such as, but not limited to, effective relief of muscular pains and stiffness of the joints; removal and/or reduction of bacteria, for example in ulcers, or acceleration of wound repair; stimulating the fibroblasts for collagen production, for stabilizing connective tissue and healing wounds, for example burns; light-induced blood vessel and lymph vessel vasodilation for possible aiding in cellulite treatment, acne and/or wrinkles; preventing and/or healing inflammation like eczema; and healing of particular skin diseases. The application of light, i.e., phototherapy, may shorten a stay in hospital after an accident or surgery and speed up the recovery, for example at home. Aesthetic therapy, for example an improvement of the skin, can also profit from phototherapy. For example, beneficial phototherapy devices are known which are provided with LEDs (Light Emitting Diodes) for emitting light to the skin and which are applied to the skin.

These types of light devices that are applied to the skin are configured from watertight material and moisture is not allowed to penetrate through the device. The light device protects the healing area from outside elements like moisture or dirt. However, this will also lead to a high humidity of the skin and the production of heat underneath the light device. This will not be beneficial for the healing process and may cause infections and bacteria to proliferate.

An object of the invention is to prevent fluids and/or heat from damaging the skin.

This object and other objects are achieved by a light device which comprises a substrate, at least one photo-organic layer, at least two electrode layers electrically separated by said at least one photo-organic layer, and at least one encapsulation layer, wherein said at least one photo-organic layer is positioned between said substrate and said at least one encapsulating layer, and wherein one or more openings spaced apart from said at least one photo-organic layer are provided through the light device to allow fluids and/or heat to pass through.

In a light device according to the invention, air can ventilate through the openings and allow fluids and/or hot air to pass through so as to remove fluids and/or heat from the skin. The inventor has recognized that, in specific cases, it is more beneficial to let fluids and/or gasses escape from the skin than to protect the skin from fluids and gases from the outside. Also, the inventor has recognized that it is possible to perforate the light device even though the emitting light source comprises photo-organic material, which in itself is unsuitable for perforation.

When air is allowed to pass through the openings, heat that is transferred to the skin by the OLEDs can escape via a neighboring skin part that lies below an opening. Also, moving the skin and/or light device provides a kind of 'pumping' effect through the openings.

In this description, the term "photo-organic layer" denotes at least an OLED layer, organic photovoltaic layer, or a layer of a similar organic material and/or construction. Since these layers have similar characteristics, wherein current is converted into light and/or vice versa (OLEDs are capable of both), the scope of the invention encompasses all such layers.

An embodiment of the invention interrupts the photo-organic layer at areas where the openings are positioned, the photo-organic layer being sealed by at least one other layer such that it is not damaged by gases and/or fluids passing through and/or over the openings.

Said object and other objects are also achieved by a method of manufacturing a light device, wherein a first electrode layer is provided on a substrate and interrupted at perforation areas, at least one photo-organic layer is provided on said first electrode layer and/or said substrate and interrupted at the perforation areas, a second electrode layer is provided covering the at least one photo-organic layer and electrically separated from the first electrode layer, at least one encapsulation layer is provided covering the at least one photo-organic layer and the electrode layers, and the lighting device is perforated at the perforation areas.

In this description, identical or corresponding parts have identical or corresponding reference numerals. The exemplary embodiments shown should not be construed to be limitative in any manner and serve merely as illustration.

Figure 1B:
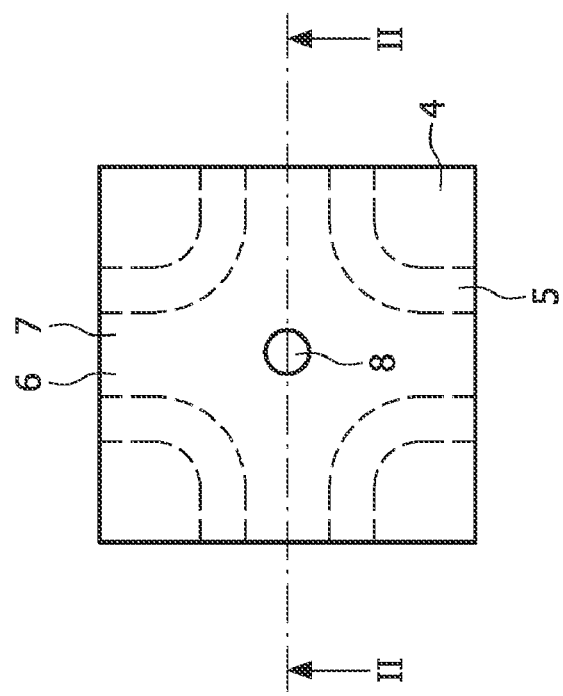
FIG. 1B is a plan view of another embodiment of a light device.
Figure 1A:
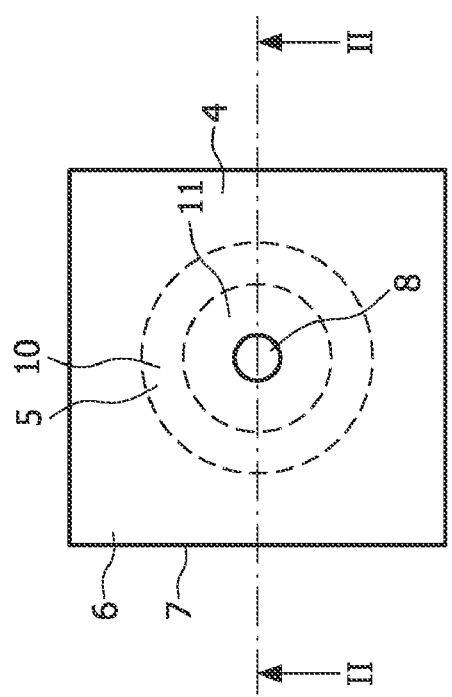
FIG. 1A is a plan view of an embodiment of a light device.
Figure 2A:
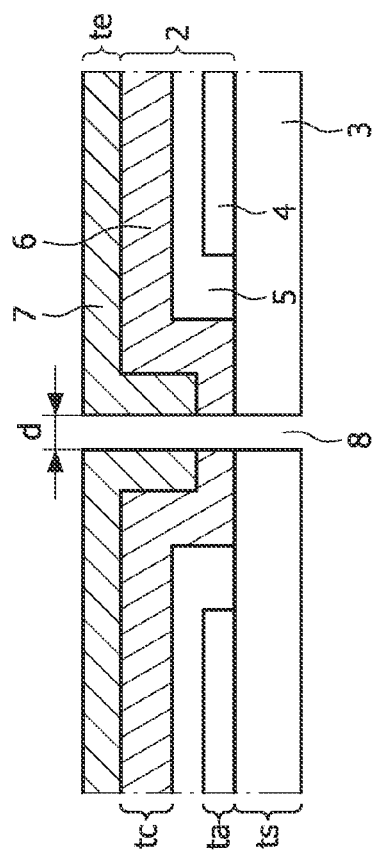
FIG. 2A is a cross-section taken through FIG. 1A or 1B.

An embodiment of a light device 1 is shown in part, in plan view in FIGS. 1A and 1B and cross-sections thereof are shown in FIG. 2A. The light device 1 comprises a light source 2 that is arranged between a thin-film encapsulation layer 7 and a substrate 3. The light source 2 comprises an anode 4, an OLED (Organic Light Emitting Diode) layer 5, and a cathode 6. As can be seen from FIG. 2A, the anode 4 is covered by the OLED 5, which in its turn is covered by the cathode 6 such that the OLED 5 electrically separates the anode 4 and the cathode 6. An opening 8 extends through the light device 1, more specifically through the substrate 3, the cathode 6, and the encapsulation layer 7 and spaced apart from the anode 4 and the OLED 5.

The light device 1 can be placed on a body part and emit light, at least in the direction of the body, for example for applying phototherapy, to enhance a healing process, or for cosmetic purposes. Preferably, the light device 1 is relatively flexible such that it conforms to an exterior part of the human body. The light source 1 may be flexible or at least partly conformable to the human body. Also the light source 1 may be constructed of several hard segments which can be moved with respect to each other, thus providing a shapeable surface. Preferably, the light source 1 is flexible over its entire surface such that it can be shaped substantially as conveniently as bandages and/or plasters.

It is advantageous when body fluids, for example perspiration, are able to pass through the openings 8. Other fluids, which may be present, for example, in wounds or may have come from outside the body, are also able to escape. This may prevent inflammation and enhance the healing process even further. To allow fluids to escape more easily, an embodiment of the light device 1 is configured to be kept at a small distance at the location where the healing has to take place.

For example, the light device 1 is kept at a distance from the skin or wound, not touching the skin or wound, for example to prevent inflammation. The light device 1 may be kept, for example, at a distance of approximately 0.1 mm from the skin and/or wound up to approximately 50 mm, preferably between approximately 2 and 30 mm, for example to let enough air pass by the wound. The light device 1 may comprise spacers for setting this distance. These spacers may comprise, for example, spots of adhesive, a soft porous layer, a gauze, etc.

Usually, the OLED 54 behaves as a thermal isolator which can also dissipate some energy towards the skin. If the surfaces do not allow a good air flow, this results in a continued heating. Therefore, in an advantageous embodiment, thermal heating is reduced by allowing air to be refreshed. In a further aspect, the light device 1 may be provided, for example, with additional cooling channels.

In an embodiment, the substrate 3 comprises a glass material having a thickness $t_s$ of, for example, approximately 2 mm. In other embodiments the substrate 3 comprises sections that may be fairly rigid but are able to move with respect to each other, thereby obtaining a relatively flexible structure. The substrate 3 may also comprise a metal material, or may be partly metal, partly glass. A substrate 3 at least partly made from metal can be configured to be relatively rigid, flexible, and/or reflective. If metal is predominantly used, an embodiment of the light device 1 is transparent towards the opposite side of the substrate 3. Hence, the top electrode is transparent, for example ITO being used as the top electrode material.

In the embodiment of FIG. 2A, the anode 4 is preferably transparent, for example made from ITO (indium-tin oxide). The thickness $t_a$ of the anode layer is, for example, 150 nm. As can be seen from FIG. 2A, the anode 4 is interrupted near a perforation area 9. Various production methods may be used for providing these interruptions during or after the application of the anode 4 to the substrate 3. In an advantageous embodiment, the interruptions comprise holes 10. For example, an anode layer comprising holes 10 may be applied by means of sputtering techniques. Holes 10 may also be applied after the anode layer was provided, for example by means of lithography or etching techniques, or a combination thereof. The anode 4 may be formed, for example, as a continuous surface with holes 10 as shown in FIG. 1A, and/or multiple surfaces may be formed such that the perforation areas 9 are positioned between the multiple surfaces as shown in FIG. 1B. In the latter embodiment the anode areas are of course interconnected by means of a circuit, which is not shown in the Figure.

In the embodiment shown, the OLED 5 is applied on top of the anode 4. The OLED 5 extends over the lateral edges of the anode 4 to achieve an electrical separation of the electrodes. In a known manner, the OLED 5 comprises, for example, organic sub-layers of a hole transport layer and a light-emitting polymer layer, for example with a thickness $t_h$ of 100 nm and 80 nm, respectively. An OLED 5 comprising substantially small molecules may comprise sub-layers of a hole-injecting, emitting, blocking and electron transport layer. This type of OLED 5 may be advantageously be provided, for example, by vapor deposition.

To prevent moisture damaging the OLED 5 and degrading the life and/or electrical performance of the OLED 5, the latter is interrupted near the perforation areas 9. In an advantageous embodiment, these interruptions are formed by holes 11. The OLED layer is preferably formed as a continuous surface with holes 11, wherein light is emitted substantially over the entire surface, interrupted by relatively small holes 11. Multiple OLED patterns may also be applied such that the perforation areas 9 are positioned between the multiple surfaces.

In another embodiment, the interruptions of the OLED 5 and/or anode 4 are configured such that an inactive area of the OLED and/or anode material is not removed near the openings 8. Electrically inactive OLED and/or anode material can be separated from the electrically active material in that material is removed from between them such that they are not electrically connected.

The cathode 6 extends on top of the OLED 5. The cathode 6 is made, for example, of a thin-film metal material known to those skilled in the art. It may also be transparent, for example made of a thin metal and/or a stack of metals such as LiF, Al, ZnSe, and/or ITO, for example 1 nm LiF, 1.5 nm Al, 10 nmAg, 30 nm ZnSe and/or ITO. The thickness $t_c$ of the cathode 6 is, for example, of the order of 100 nm. In the embodiment shown in FIG. 2A, the cathode 6 extends over the top surface and lateral edges of the OLED 5 up to the openings 8. In this way any possible oxidation of cathode material will be limited to a relatively small area and will not reach the OLED 5. In this embodiment, the cathode 6 can be applied relatively simply and then be perforated afterwards. The cathode 6 may also serve as a seal between the encapsulation layer 7 and the substrate 3, sealing off the OLED 5.

In principle, a light device 1 may have the cathode 6 and anode 4 interchanged compared with the embodiment of FIG. 2A, i.e. with the cathode 6 on the substrate 3 and the anode 4 on top.

The encapsulation layer 7 extends on top of the cathode layer 6 and is configured to shield off moisture and/or gases from its surface. The encapsulation layer 7 may extend substantially over the layers below up to the openings 8. In an exemplary embodiment, the encapsulation layer 7 has a thickness $t_e$ of approximately 10 μm of which, for example, 0.6 μm is sealing material and the rest is protective coating. The encapsulation layer 7 preferably comprises a thin-film encapsulation layer.

In an embodiment, the encapsulation layer 7 comprises a NONON (N=nitride, O=oxide) stack or the like, as described in patent application WO2003050895, which is incorporated by reference herein. This type of encapsulation layer 7 comprises stacked sub-layers of dielectric materials, a first and third sub-layer preferably being silicon nitride and the second sub-layer being preferably selected from among silicon oxide, silicon oxynitride, silicon oxidefluoride, titanium oxide, tantalum oxide, zirconium oxide, hafnium oxide, aluminum oxide, or any mixture thereof.

In an embodiment, the thickness of the light source 2 is approximately 200 μm.

Figure 2B:
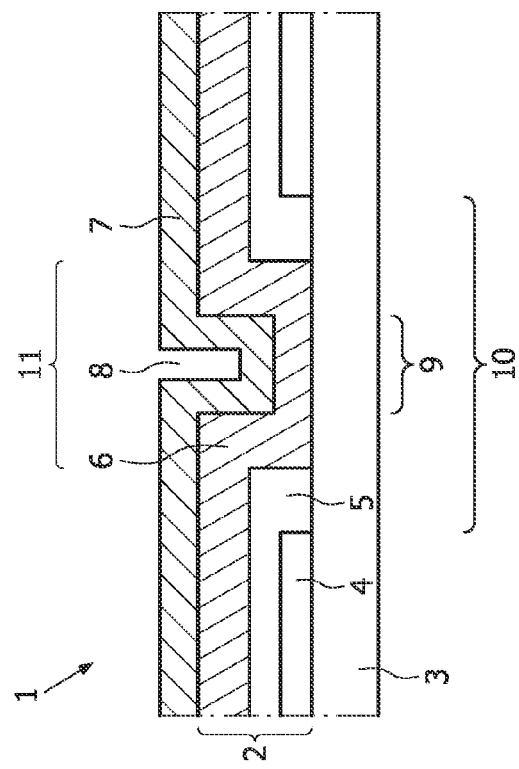
FIG. 2B is a schematic cross-section of an embodiment of a light device before the light device is perforated.
Figure 3A:
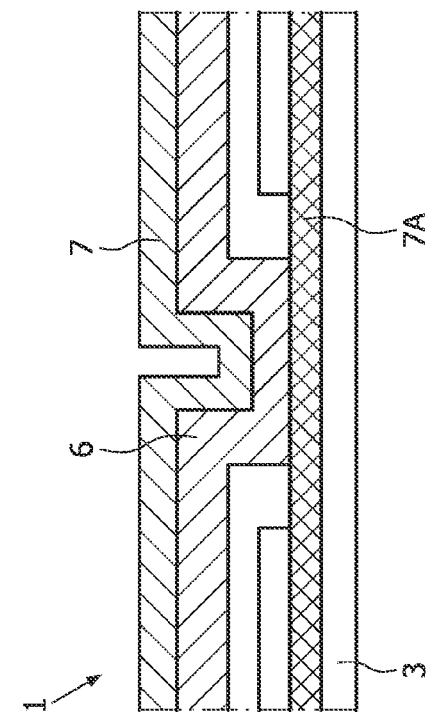
FIG. 3A is a schematic cross-section of an embodiment of a light device.
Figure 3B:
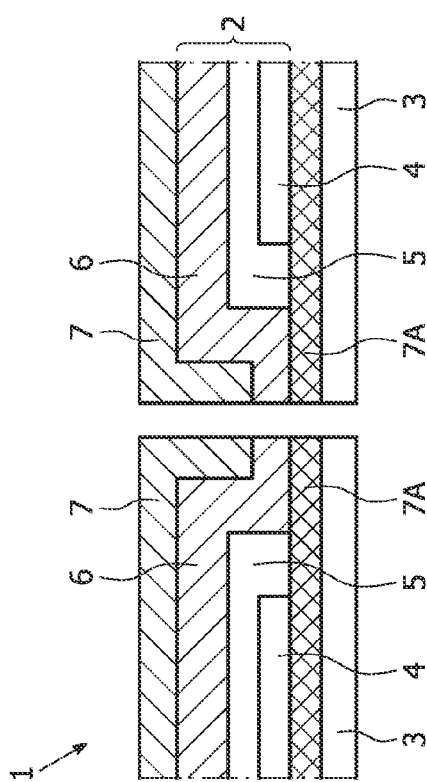
FIG. 3B is a schematic cross-section of an embodiment of a light device before the light device is perforated.

In an embodiment of a method according to the invention, the cathode 6 and/or the encapsulation layer 7 can be deposited on top of the layers, as shown in FIGS. 2B and 3B, by any suitable production method and are perforated with openings 8 afterwards, such that the interrupted anode 4 and OLED 5 are isolated from the openings 8, i.e. sealed off by the cathode 6 and/or the encapsulation layer 7.

Various production methods may be suitable for perforating the light device 1 with openings 8, depending on the materials used in the light device 1, particularly the OLED material. A $CO_2$ laser may be used, which may make, for example, openings 8 with a diameter d of approximately 40 μm. Other ways of perforation include, for example, perforation by needles or pins; mechanical, spark, sand, water or laser drilling; wet or dry etching; etc.

In an advantageous embodiment, a synthetic resin substrate 3 is used as shown in FIGS. 3A and 3B. With some synthetic resin materials it is difficult to stop moisture from penetrating through a synthetic resin substrate 3 made thereof. For that reason, an additional encapsulation layer 7A may be applied, sealing off the above layers from moisture. Synthetic resin substrates 3, for example made from polyimide, can be made to be relatively freely shapeable, thin, flexible, and transparent.

Figure 4:
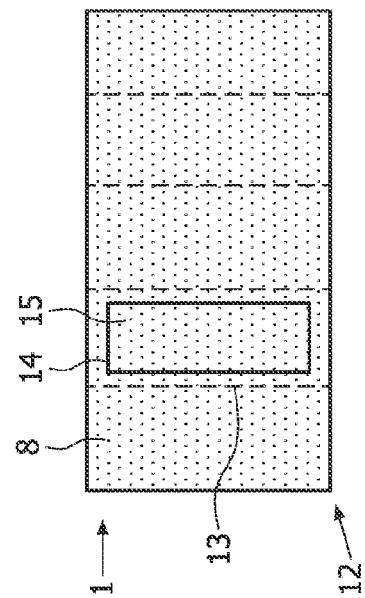
FIG. 4 is a schematic plan view of an embodiment of a light device.

An advantageous example of an embodiment of a light device 1 according to the invention is schematically illustrated in FIG. 4. The light device 1 as shown in FIG. 4 is configured to be a sheet 12 comprising multiple light devices. Before usage a light device 1 can be cut off from the sheet 12, for example near a cutting line 13. A plaster 11 may also be torn off from the sheet 12, wherein the line 13 is a perforated line 13 or some other type of line 13. Preferably, no OLED 5 is present near the line 13, so that it will remain sealed off. Also, the anode 4 may be configured such that lines 13 do not cross an anode layer. In this embodiment, for example, relatively large separating areas of the substrate 3 are not covered by the anode 4, so that the substrate 3 can be separated between the anodes 4. For example, drawn lines 13 may be put on separating areas to indicate where to separate a light device 1 from the sheet 12. In an advantageous embodiment, the openings 8 may be conveniently used to tear off a part of the multiple light device sheet 12, while the OLED 5 is already sealed off from the openings 8, as in the embodiment shown in FIG. 1B. Of course, it is also possible, for example, to cut or tear off a light device 1 without using a line 13. The sheet 12 and the separated light devices 1 can be designed into any shape and/or form. This makes it possible, for example, to pre-shape the light device 1 for covering large as well as small parts of the body in places that are easy or difficult to reach. In this way it is possible to treat large back burns as well as small facial wrinkles, for example, by means of the same sheet 12 or parts thereof.

A battery or power supply 14 of the light device 1 may be about as thin as the lighting device itself. The battery 14 may be a re-changeable battery 14, so that it is possible to re-use the battery 14 multiple times, or it may be integrated with the light device 1, depending on the preferred type and/or usage. The battery 14 may be any type of battery 14, for example a chemical type of battery 14, but also, for example, a capacitor or any electrical power source that may provide an electrical current through the light device 1. Examples of electric power suppliers may be various kinds of NiMH systems. Li-ion systems and fuel cells may also be provided. For example, the 'conventional' types may be used in the case of Li-ion and also the polymer and gel type systems. Solid-state batteries may be desirable, for example because they do not leak, and these may be provided, for example, on rigid substrates or on flexible (polymer) substrates or other types of substrates. Those skilled in the art it will appreciate that multiple power sources may be suitable within the scope of the invention.

In a preferred embodiment, lithylene batteries 14, preferably rechargeable, are used for the light device 1. Advantageously, these systems can be preshaped and fully integrated into the synthetic resin and/or electronic housing of practically any shape. This type of battery 14 can be given any desired shape in principle and have a thickness of, for example, approximately 1 mm. The power supply may be approximately 3.8 V and the lithylene batteries may, for example, be connected in series to increase the voltage if higher brightness levels are commercially or therapeutically interesting. A typical lithylene battery 14 can supply, for example, approximately 1200 mAh and supply a polyled having a surface area of approximately 100 cm$^2$ and emitting light at approximately 50 Cd/m$^2$ with electric current for approximately 24 hours with an efficiency of approximately 10 cd/A.

One of the advantages of lithylene batteries 14 is that these batteries 14 can be easily stacked, so that the operating time of the light device 1 can be extended. Furthermore, lithylene batteries 14 allow an advantageous freedom in design, and the battery 14 may, for example, be perforated and be positioned on top of the light device 1. As shown in FIG. 4, an embodiment of a light device 1 comprises a battery 14 wherein holes 15 are provided that correspond with openings 8. The battery holes 15 are patterned in the same way as the openings 8, such that body fluids and/or gases can pass through.

The combination and/or connection of the battery 14 and the light device 1 is preferably relatively solid and will stay connected to the skin during heavy movement, for example in sports, and/or when it bumps against objects and/or when it is caught between loads, for example when a person sits on the light device 1.

In certain aspects the battery 14 may be fixedly connected and/or integrated with the light device 1, for example, so that it may be disposed together with the light device 1 after usage. Also the light device 1 might be provided with electricity by other means than a battery 14, such as the local electrical network, solar energy, induction charging etc.

In another aspect, the light device 1 can be worn as a body cover and therefore is configured to be at least partly flexible. The light device 1 can be configured such that it is used as a plaster, bandage, or piece of clothing. Similar elements as used in plasters, bandages, or clothes can be integrated with the light device 1. For convenient use, for example for home users, the light device 1 is configured to be disposable, i.e. made of cheap, relatively light materials and/or configured for relatively short use.

In an embodiment, the light source 2 comprises at least one polymer solar cell 2, i.e. an organic photovoltaic device 2. These devices 2 have a similar construction and characteristics as OLED light devices 2, generally speaking an organic layer 5 between two electrodes 4, 6, and the above description may be applied analogously to organic photovoltaic devices 2 configured to convert light into electricity. Here, the solar cells 2 may, for example, be conveniently applied in combination with a substrate 3 that is at least partly made of metal. Applications for a light device 1 comprising organic photovoltaic devices 2 include, for example, applications for outdoor sports, Global Positioning Systems, radios, etc. Combinations of organic photovoltaic devices 5 with OLEDs 5 may also be configured, for example the light device 1 comprising an organic photovoltaic device 5 that supplies power to the light device 1 comprising the OLED 5.

In another embodiment, different OLEDs 5 are applied, for example with different wavelengths. Furthermore, a wavelength, intensity, and/or temperature control may be connected to the light device 1 so that preferred color settings corresponding to the preferred healing method can be applied.

Obviously, words such as "top" or "bottom" are merely used for reference purposes, referring to the positions in the drawings. Devices according to the present invention can be applied and used in any desired orientation.

It will be obvious that the invention is not limited in any manner to the exemplary embodiments that are represented in the description and the drawings. Many variations and combinations are possible within the framework of the invention as outlined by the claims. Especially combinations of aspects and embodiments as shown are considered to be disclosed herein. The Figures are not necessarily true to scale, for example thicknesses may have been exaggerated for the sake of clarity. All comparable variations are understood to fall within the scope of the invention as outlined by the claims.

The invention claimed is:

1. Light device comprising:
a substrate;
a first planar electrode layer disposed on the substrate;
a photo-organic layer having a top surface portion disposed on the first planar electrode layer in a first plane and furthermore having an emission portion formed at a boundary of the top surface portion such that the emission portion protrudes beyond the first planar electrode layer, wherein the emission portion includes a lateral edge surface disposed in a second plane that is transverse to the first plane;
a second planar electrode layer that is electrically separated from the first planar electrode layer by the photo-organic layer, wherein the second planar electrode layer is disposed on the photo-organic layer such that the second planar electrode layer protrudes beyond the emission portion of the photo-organic layer, and wherein the second planar electrode layer is further disposed such that the second planar electrode layer covers the lateral edge surface of the emission portion of the photo-organic layer; and
at least one encapsulation layer,
wherein the photo-organic layer is positioned between said substrate and said at least one encapsulating layer, and wherein multiple openings spaced apart from the photo-organic layer are provided through the light device to allow fluids and/or heat to pass through.

2. Light device according to claim 1, wherein the photo-organic layer is interrupted at the area of the openings and is sealed off from said openings by at least one of said at least one encapsulation layer and/or at least one of the first planar electrode layer and the second planar electrode layer.

3. Light device according to claim 1, wherein the openings are configured to pass through at least the substrate and the at least one encapsulation layer.

4. Light device according to claim 1, wherein the openings are configured to pass through at least one of the first planar electrode layer and the second planar electrode layer.

5. Light device according to claim 1, wherein one of the first planar electrode layer and the second planar electrode layer is a cathode layer which covers said photo-organic layer, and wherein one of the first planar electrode layer and the second planar electrode layer is an anode layer which is covered by said photo-organic layer.

6. Light device according to claim 1, wherein at least one encapsulation layer comprises stacked sub-layers of dielectric materials, wherein a first and a third sub-layer are based on silicon nitride and a second sub-layer between said first and third sub-layers is selected from among silicon oxide, silicon oxynitride, silicon oxidefluoride, titanium oxide, tantalum oxide, zirconium oxide, hafnium oxide, aluminum oxide, or any mixture thereof.

7. Light device according to claim 1, wherein a power supply is provided, the power supply comprising a lithylene battery with corresponding openings.

8. Light device according to claim 1, wherein at least one tear-off area is provided comprising a weakened element, comprising openings or grooves, wherein the tear-off area is configured such that no photo-organic layer is present in said tear-off area.

9. Light device according to claim 1, wherein the substrate is substantially made of glass and/or metal.

10. Light device according to claim 1, wherein said photo-organic layer and the first planar electrode layer and the second planar electrode layer extend between at least two encapsulation layers.

11. Light device according to claim 10, wherein the substrate is substantially made from synthetic resin.

12. Light device according to claim 1, wherein the light device is at least substantially flexible and/or conformable to a body part.

13. Light device according to claim 1, wherein the photo-organic layer comprises at least one OLED layer and/or organic photovoltaic layer.

14. Method of manufacturing a light device,
disposing a first electrode layer on a substrate, wherein the first electrode layer is interrupted at perforation areas;
disposing a photo-organic layer having a top surface portion and an emission portion, the emission portion including a lateral edge surface, on said first electrode layer and/or said substrate such that the photo-organic layer protrudes beyond the first electrode layer, wherein the photo-organic layer is interrupted at the perforation areas;
disposing a second electrode layer is on the photo-organic layer such that the second electrode layer protrudes beyond the emission portion of the photo-organic layer and such that the second electrode layer covers the lateral edge surface of the emission portion of the photo-organic layer, wherein the second electrode layer is electrically separated from the first electrode layer;
disposing an encapsulation layer covering the photo-organic layer and the first and second electrode layers;
perforating the lighting device at the perforation areas.

15. Method according to claim 14, wherein a second encapsulation layer is disposed on the side opposite to the encapsulation layer, such that the photo-organic layer and the first electrode layer and second electrode layer extend between the encapsulation layers.

16. Method according to claim 14, wherein the device is perforated using a $CO_2$ laser.

17. Method according to claim 14, wherein the photo-organic layer comprises at least one OLED layer and/or organic photovoltaic layer.

* * * * *